United States Patent
Lindahl et al.

(10) Patent No.: US 6,979,454 B1
(45) Date of Patent: Dec. 27, 2005

(54) BIOLOGICALLY ACTIVE COMPOSITION

(75) Inventors: Åke Lindahl, Skurup (SE); Rickard Bryland, Malmö (SE)

(73) Assignee: Jagotec AG, Muttenz (CH)

( * ) Notice: Subject to any disclaimer, the term of this patent is extended or adjusted under 35 U.S.C. 154(b) by 0 days.

(21) Appl. No.: 09/155,642

(22) PCT Filed: Apr. 29, 1997

(86) PCT No.: PCT/SE97/00721

§ 371 (c)(1),
(2), (4) Date: Oct. 2, 1998

(87) PCT Pub. No.: WO97/40818

PCT Pub. Date: Nov. 6, 1997

(30) Foreign Application Priority Data

Apr. 30, 1996 (SE) .................................. 9601665

(51) Int. Cl.[7] .................. A01N 25/08; A01N 45/00; A61K 9/00; A61K 31/585; A61K 31/56
(52) U.S. Cl. ................. 424/409; 424/401; 424/445; 424/484; 424/400; 514/175; 514/180; 514/168; 514/762; 514/887; 514/947
(58) Field of Search ............... 424/401, 445, 424/409, 484, 400; 514/762, 887, 947, 175, 514/180

(56) References Cited

U.S. PATENT DOCUMENTS

| | | | |
|---|---|---|---|
| 4,299,828 A | | 11/1981 | Wang et al. |
| 4,552,872 A | * | 11/1985 | Cooper et al. .............. 514/175 |
| 4,711,906 A | | 12/1987 | von Stetten et al. |
| 5,174,995 A | | 12/1992 | Davis |
| 5,362,497 A | * | 11/1994 | Yamada et al. ............. 424/443 |

* cited by examiner

Primary Examiner—Shengjun Wang
(74) Attorney, Agent, or Firm—Mintz Levin Cohen Ferris Glovsky and Popeo, P.C.

(57) ABSTRACT

A biologically active stick composition comprising a biologically active agent dissolved in a carrier system including an unsaturated fatty acid alcohol in mutual dissolution with an alkylene glycol as a solvent for said biologically active agent and a stiffening agent therefor, said stiffening agent imparting stick consistency to the composition, said alkylene glycol preferably being present in an amount of more than 12%. The composition can be prepared by dissolving the active agent in the solvent, combining the solution with the stiffening agent and shaping the formulation into a stick. The composition is especially intended for use as a medicament, preferably in the treatment of dermatological conditions, where it has been found to possess outstanding bioavailability properties.

40 Claims, No Drawings

BIOLOGICALLY ACTIVE COMPOSITION

This application is a 371 of PCT/SE97/00721, filed Apr. 29, 1997, which claims foreign priority of SWEDEN 9601665-4, filed Apr. 30, 1996.

TECHNICAL FIELD

The present invention relates to the field of biologically active compositions and, in particular, to a biologically active stick composition. Preferably the invention relates to pharmaceutical compositions but, other applications outside the medical field are possible within the scope of the invention.

The invention also relates to the use of such compositions as medicaments and for the manufacture of stick medicaments for treating dermal conditions, as well as to a process for the preparation of such compositions.

BACKGROUND OF THE INVENTION

One of the problems associated with topical medical treatment with high potency drugs is in the application of the composition. Most compositions intended for dermatological treatment of the skin are based on cream, ointment of gel vehicles and, when these are applied to the skin, the incidence of extralesional treatment can be substantial; areas surrounding the lesion to be treated as well as the fingers used to apply a product can be affected by the drug.

By using stick compositions having higher viscosities, which can be housed within a protective package, such extralesional treatment can be avoided or at least substantially eliminated. Another advantage of stick formulations is that, by their use, it is simple to achieve a uniform distribution of drug over the lesion to be treated.

Stick based products are not novel in the treatment of skin conditions and several active compounds have been formulated into sticks. Stick compositions, as herein referred to, are formed from erodible, usually soft and waxy materials having a solid consistency. When rubbed across the skin, such compositions are eroded and deposit a coating of their constituent material on the skin. Generally, stick compositions include mixtures of lipids and surfactants as carriers.

A major drawback of those stick compositions used today, however, results from the fact that many drugs, at best, are only marginally soluble in their lipid based formulations and, therefore, must be incorporated into stick compositions as suspended solid particles. This, however, leads to several disadvantages, the most serious one being sedimentation of the active ingredient during manufacture. The method used to manufacture stick compositions involves heating, mixing, packing and cooling and, during, the heating, mixing and cooling steps, the viscosity of the lipid mixture can be sufficiently low to allow the suspended active drug to settle. The resulting sedimentation of the active ingredient reduces the homogeneity of the composition and can prevent the product from meeting the standards required for pharmaceutical products.

Several solutions to the sedimentation problem have been proposed. Some are based on mechanical measures, which involve regularly turning any vessel used to accomodate the composition before it has set, so that the drug particles are maintained in a suspended state. Others involve the addition of thickening agents to form thixotropic gels. None of these proposals, however, have enabled the manufacture of homogeneous formulations in a reproducible way.

Another disadvantage with topical formulations in general, and stick formulations in particular, is the poor bioavailability of the active drug to the skin. For topical dermatological formulations containing corticosteroides, bioavailability can be in the order of a few percent. Low bioavailability has many implications. One is that the effect of a drug can be variable and non-reproducible, both at the site of application and systemically. Another is that, when conditions at the site of application are favourable for the penetration of a drug, systemic concentrations thereof can reach toxic levels.

A corticosteroid stick product containing propylene glycol or 1,3-butylene glycol is previously known from U.S. Pat. No. 4,299,828. However, said product is not based on the use of an unsaturated fatty acid alcohol as a solvent and the alkylene glycols referred to are not utilized as solvents but rather as anti-microbial compounds. Furthermore, it is specifically stated that said anti-microbial compound is not dissolved in the stick but dispersed therein (col 3 lines 35–40 and claim 1), i.e. the stick is not a homogeneous product. In addition thereto the preferred percentage of the alkylene glycol is disclosed as 2–10 and optionally 3–8% by weight (col 3 lines 20–22 and claim 1). Thus, the purpose of the alkylene glycol is completely different from that of the present invention where higher percentages of alkylene glycol have been found to give other effects than those referred to in U.S. Pat. No. 4,299,828.

DESCRIPTION OF THE INVENTION

The present invention relates to a completely novel solid composition, especially a stick composition, for biologically active agents, which may seem similar to the aforementioned lipid based stick products, but which is of a completely different structure and thereby possessed of completely different properties as compared thereto.

More specifically, the solid compositions according to the present invention do not rely upon mechanical means to ensure uniform distribution of the biologically active agent. The active agent is distributed in a lipid carrier, but not in a suspended or dispersed state as previously practised but, rather, in a dissolved state. Thus, it has unexpectedly been found that, in spite of the generally poor solubility of the biologically active compounds previously formulated in stick compositions, a more or less complete dissolution of the biologically active agent can be obtained by means of the present invention into a completely homogeneous solid composition.

A first object of the invention is to provide a composition which contains a biologically active agent in a dissolved state.

Another object of the invention is to provide a composition which possesses an enhanced stability against sedimentation of the active agent.

Still another object of the invention is to provide homogeneous compositions.

One other object of the invention is to provide compositions possessing an enhanced release rate for the active agent, i.e. improved bioavailability, especially for use in dermatology.

Still another object of the invention is to provide compositions, the consistency of which can be controlled by means of the composition thereof, especially to accomplish a composition to be administered via the skin.

One other object of the invention is to provide a composition for use as a drug or medicament, especially for the treatment of dermatological conditions.

Still another object of the invention is to provide a process for the preparation of compositions, especially stick compositions of the type referred to above.

Still other objects of the invention should be obvious to a person skilled in the art after having studied the following description of the invention.

Thus, according to a first aspect of the present invention there is provided a solid composition comprising a biologically active agent dissolved in a carrier system, wherein the carrier system includes a specific combination of solvents for the active agent and a stiffening agent for imparting a solid consistency to the composition. Preferably, the stiffening agent is a viscosity enhancing agent capable of imparting a soft and erodible consistency to the composition.

It is preferred that compositions in accordance with the present invention are stick compositions as hereinbefore defined.

More specifically a solid composition is claimed, wherein the carrier system includes an unsaturated fatty acid alcohol in combination with an alkylene glycol selected from propylene glycol, butylene glycol, dipropylene glycol and/or dibutylene glycol as a solvent for the active agent and a stiffening agent for imparting a solid consistency to the composition, said alkylene glycol being present in an amount that gives mutual dissolution with said unsaturated fatty acid alcohol as well as dissolution of said active agent.

By employing the present invention, it is possible to combine the good characteristics of a homogeneous solution with the good characteristics of a stick products, which combination has hitherto not been possible.

As the carrier system preferably comprises miscible solvent and viscosity enhancing substances, compositions in accordance with the invention can form stable stick compositions without any substantial sedimentation of the biologically active agent.

Furthermore, the solvent combination used should be capable of dissolving the biologically active agent at a temperature where significant decomposition of said agent is avoided.

Generally, the biologically active agent is any biologically active compound, or mixture of compounds, which can be dissolved to a substantial extent in the carrier system of the present invention. Typically, this means that the biologically active agent is a lipophilic, i.e. lipid soluble, compound. In this context the invention is of special interest in connection with drugs or medical compounds but, of course, the inventive idea is applicable to any biologically active agent for which a stick formulation is appropriate. The term "biologically active agent" should be interpreted in a broad, conventional sense to mean an element, compound or composition which, when present in an effective amount, will interact with living organisms, preferably to elicit a therapeutic effect.

There are a large number of agents falling within the above-mentioned definitions and which can be formulated in compositions according to the invention. However, some specific examples include steroids, e.g. corticosteroids, vitamins, sex hormones, biologically active lipids, fatty acids, antibiotics or antimicrobials and local anestetics. In this connection it should be noted that, as is common in the art, the compounds can be used per se or in the form of salts or esters or other chemically modified forms thereof.

Some examples within the above-mentioned groups include vitamins A, D2, D3, E, K and derivatives thereof, androgens, estrogens and derivatives thereof, amide type local anestetics and antimicrobials such as antivirals, antibacterials, antiprotozoals and antifungals. Further examples include fluocinonide, omega-3-fatty acid and azelaic acid, and salts and esters thereof, clobetasol, and salts and esters thereof, and betamethasone and salts and esters thereof, particularly betamethasone-17-valerate and betamethasone-dipropionate.

Generally the solvent used is capable of dissolving the specific active agent used to the desired extent. Preferably the solvent comprises an unsaturated $C_{16}$–$C_{20}$-fatty acid alchol, more preferably $C_{18}$-fatty acid alcohol, in mutual dissolution with the alkylene alcohol referred to. In the case of said unsaturated $C_{18}$-fatty acid alcohol, it is preferably selected from oleyl alcohol, ricinolyl alcohol, linolyl alcohol and/or linolenyl alcohol and more preferably is oleyl alcohol. Another example of a $C_{18}$-fatty acid alcohol is eleosteryl alcohol, while a preferable example of a $C_{16}$-fatty acid alcohol is palmitoleyl alcohol, and a preferable example of a $C_{20}$-fatty acid alcohol is arachidonyl alcohol.

In more general terms the unsaturated fatty acid alcohol is used in combination with an alkylene glycol having the general formula $R(OH)_2$; a di- or poly-alkylene glycol having the general formula $HOR(OR)_nOROH$; a $C_4$–$C_{36}$ (e.g. $C_4$–$C_{18}$) aliphatic primary alcohol; or a mixture of two or more such compounds. In the foregoing formulae, each group R can be the same or different and is an alkyl, preferably a $C_2$–$C_6$ alkyl group and $n \geq 0$. Preferred groups R are ethyl, propyl and butyl groups and the preferred glycols thus include propylene glycol, butylene glycol, dipropylene glycol and dibutylene glycol.

In addition to the above-mentioned unsaturated fatty acid alcohols other primary alcohols can be included in the composition, such as lauryl alcohol, myristyl alcohol, palmityl alcohol and/or stearyl alcohol.

In one preferable embodiment of the invention an additional solvent can be included wich is selected from lipid esters, such as fatty acid esters and esters of sorbic acid. Examples of fatty acids from which such esters can be derived include lauric acid, myristic acid, palmitic acid, stearic acid, oleic acid, ricinoleic acid, linolic acid and linolenic acid. The precursor alcohols are preferably the $C_1$–$C_6$-alkanols methanol, etanol, propanol, butanol, pentanol and hexanol with either straight or branched carbon chains. Especially preferred esters in this respect are the propyl esters, including the isopropyl esters, especially isopropylpalmitate.

Still further additional solvents usable in the invention are the $C_2$–$C_6$ alkylene carbonates, e.g. ethylene, propylene or butylene carbonate, preferably propylene carbonate.

The viscosity enhancing agent should be chosen such that it is compatible with the solvent and so that it imparts the desired viscosity or consistency thereto. Generally this means that said viscosity enhancing agent is a waxy substance.

In preferred embodiments of the invention said waxy substance is a natural or synthetic wax which is generally defined as monoester of a long-chained (typically $C_{14}$–$C_{36}$, e.g. $C_{18}$–$C_{24}$) carboxylic acid with a long-chained (typically $C_{16}$–$C_{36}$) alcohol. In both cases the carbon chains, preferably, are unbranched aliphatic chains.

In another embodiment the waxy substance is a fat and, preferably, a triglyceride of a $C_{18}$–$C_{36}$ fatty acid or a glycol (typically an alkylene glycol as herein before defined and comprising 2–6 carbon atoms) ester of a $C_{18}$–$C_{36}$ fatty acid.

Combinations of said waxes and/or waxy substances may be employed and, in an especially preferred embodiment of the invention, the viscosity enhancing agent comprises a combination of a natural and/or synthetic wax plus a triglyceride and/or a glycol ester, as defined above, and enables the carrier system's rheological properties to be accurately tailored, for example, to achieve a broad softening point.

Other preferred waxes are paraffin wax and cerasine wax.

In some cases, the viscosity enhancing agent, or waxy substance, can cause the composition to be too viscous. In accordance with the present invention this can be avoided by incorporating into the carrier system an oil having the capacity to plasticize the viscosity enhancing agent and reduce the viscosity of the carrier system to a level that is suitable for the composition's intended purpose. Preferred plasticizing oils include low molecular weight aliphatic acids and alcohols, especially with branched chains, e.g. fluid lanoline.

When the inventive composition is for use as a medicament, it should hardly need mentioning that all of the above-identified ingredients, as well as other optional conventional further ingredients, should be pharmaceutically acceptable and non-toxic when the composition is used in the intended manner.

The combination of solvent and viscosity enhancing agent in the carrier system should be selected in line with the principles given above such that a proper dissolution rate, consistency and release rate are obtained. Generally this means that the amounts of the different ingredients could be decided experimentally using techniques well known to persons skilled in the art. However, in general the amount of solvent can be within the range of 20–85% by weight, the amount of viscosity enhancing agent can be within the range of 15–80% by weight and the amount of plasticizing oil can be within the range of 0–30% by weight, based on the total weight of the carrier system.

Preferably the amount of solvent is within the range of 25–75, more preferably 40–60, percent by weight, while the amount of viscosity enhancing agent is within the range of 15–55, more preferably 25–50, percent by weight and the amount of plasticizing oil is within the range of 0–30, more preferably 2–20, percent by weight.

As was mentioned above it has been found possible to combine the unsaturated fatty acid alcohol with the alkylene glycol in such properties that mutual dissolution of the solvents as well as full dissolution of the active agent in the composition is accomplished. Generally this means that the amount of alkylene glycol is more than 12% by weight and preferably at least 15% by weight, based on the total weight of the carrier system.

According to an especially preferable embodiment of the invention the amount of the alkylene glycol solvent, preferably propylene glycol, is within the range of 12–23, preferably 15–23, % by weight, based on the total weight of the carrier system, more preferably 12–20, especially 15–20, % by weight.

In another preferable embodiment of the invention, where said additional solvent is present, the weight ratio of oleyl alcohol: additional solvent is within the range of 1:2 to 5:1, preferably 1:2 to 3:1 and more preferably 1:2 to 2:1.

The amount of the biologically active agent is of course dependent on the effect to be accomplished. Generally, however, the upper limit will be the active agent's solubility limit in the carrier system, which can be up to 40 percent by weight or in some cases merely up to 10 or even 5 percent by weight, in all cases calculated on the weight of the carrier system. Preferably the range thereof can be 0.01–10, especially 0.02–5, percent by weight, on the same basis. The exact amount, however, is easily determined by a person skilled in the art with reference to the optimum or maximum effect it is wished to obtain.

It is especially preferred that compositions according to the invention are for pharmaceutical or medical purposes. In this case, the biologically active agent can be a therapeutic or prophylactic agent of any kind. The other ingredients employed must be selected in accordance with the general principles applying to the formulation of medical or pharmaceutical compositions.

In an especially preferred embodiment, the inventive composition comprises a medicament for administration to the skin, or for dermal administration. In such a case a person skilled in the art will formulate the composition such that its viscosity will be proper for administration in that way and such that the release of the active compound will have the desired profile.

Thus, from the above-mentioned it should be clear that stick compositions according to the present invention are especially well suited for the treatment of dermatological conditions.

According to yet another aspect of the invention there is also provided a process for the preparation of compositions, preferably stick compositions, in accordance with the invention. Said process comprises dissolving the biologically active agent in the solvent therefor, combining the resulting solution with a viscosity enhancing agent so as to impart a solid consistency to said solution and shaping the resulting formulation into a stick.

Preferably the active agent is dissolved in the solvent, or part thereof, and the solution obtained is then added to a melted mass of the viscosity enhancing agent, preferably while being stirred. When a homogeneous mass has been obtained, said mass, preferably after some cooling, can then be poured into a mould and allowed to cool and set in the desired shape. Proper temperatures in this respect are easily determined by a person skilled in the art.

The composition is physically stable below +50° C. although softening of the structure may occur. The composition should be capable of returning to its original viscosity after cooling to +30° C. or lower. This may also be valid after heating to temperatures in excess of +50° C.

After such heating followed by cooling to +30° C. or lower the composition will still be homogeneous. This is an advantage compared to such stick formulations where the active drug is in solid form, i.e. suspended. In these compositions the active drug will settle out at higher temperatures and form an unhomogeneous preparation.

EXAMPLES

The invention will now be exemplified further by means of the following non-limiting working examples.

Example 1

Stick compositions 1–10 were prepared from the following ingredients, the figures being percentages by weight.

|  | 1 | 2 | 3 | 4 | 5 | 6 | 7 | 8 | 9 | 10 |
|---|---|---|---|---|---|---|---|---|---|---|
| Fluid lanoline | 14.3 | 14.3 | 12.9 | 12.9 | 15.4 | 16.7 | 17.6 | 17.6 | 18.5 | 11.9 |
| Paraffin wax | 7.1 | 7.1 | 6.4 | 6.4 | 5.4 | 3.5 | 3.7 | 3.7 | — | 5.8 |
| Ceresine wax | 5.4 | 5.4 | 4.9 | 4.9 | 5.8 | 4.7 | 4.9 | 4.9 | 3.9 | 4.5 |
| Syncrowax ERLC | 14.3 | 14.3 | 12.9 | 12.9 | 8.6 | 7 | — | — | — | 11.9 |
| Syncrowax HGLC | 10.7 | 10.7 | 9.6 | 9.6 | 12.9 | 11.7 | 14.7 | 14.7 | 15.5 | 8.9 |
| Oleyl alcohol | 35.6 | 35.6 | 32 | 32 | 38.4 | 41.7 | 43.7 | 43.7 | 46 | 29.7 |
| Isopropylpalmitate | 12.5 | 12.5 | 11.2 | 11.2 | 13.5 | 14.6 | 15.4 | 15.4 | 16.1 | 10.4 |
| Propylene glycol | — | — | 10 | 10 | — | — | — | — | — | 16.7 |
| Clobetasol propionate | 0.05 | — | — | — | — | — | — | — | — | — |
| Betamethasone-valerate | — | 0.12 | — | — | — | — | — | — | — | — |
| Fluocinonide | — | — | 0.05 | — | — | — | — | — | — | — |
| Betamethasone-dipropionate | — | — | — | — | 0.067 | 0.067 | 0.067 | — | 0.067 | 0.067 |

The manufacturing process was as follows:

The active agent was dissolved in the oleyl alcohol. Separately the lanoline, paraffin wax, ceresine wax, glycol esters, triglycerides and the isopropyl palmitate were mixed together in a glass beaker.

The mixture in the glass beaker was then heated to about 75° C. and was allowed to melt while being stirred. The oleyl alcohol and active agent solution, also heated to +75° C., was then added thereto and the combination was stirred for 10 minutes.

After reducing the temperature to about 65° C. the resulting composition was poured into a stick mould and allowed to cool and solidify.

These compositions were then tested by means of conventional blanching tests (blanching is an established method of assaying biological activities of steroid preparations) and compared with commercial creams and ointments. The results of said tests are summarized as follows:

| Product | Test mean value |
|---|---|
| Comp. 1 | 1.78 |
| 2 | 1.25 |
| 3 | 1.81 |
| 4 | — |
| 5 | 1.69 |
| 6 | 1.67 |
| 7 | 1.33 |
| 8 | 0.03 |
| 9 | 1.47 |
| 10 | 2.53 |
| Lidex Ointment[x] | 2.42 |
| Temovate Ointment[xx] | 2.75 |
| Betamethasone valerate Ointment (Fougera)[xxx] | 1.94 |
| Diprolene Cream | 2.64 |
| Diprolene Ointment | 2.72 | x) 0,05% fluocinonide
xx) 0,05% clobetasol propionate
xxx) 0,12% betamethasone valerate From said results it can be seen that composition No. 10 according to the invention was bioequivalent to all commercial cream and ointment products, which is indeed unexpected and means a great contribution to the art now that a stick product can compete with well-established creams and ointments. Furthermore, it should be borne in mind that the new stick claimed possesses great advantages also compared to known stick products as has been described above (completely homogeneous product with no sedimentation problems, etc.).

What is claimed is:

1. A solid dermatological composition comprising a biologically active agent dissolved in a homogeneous carrier system, wherein the carrier system consists essentially of:
   (a) 20–85% by weight of a solvent comprising (i) an unsaturated $C_{16}$–$C_{20}$-fatty acid alcohol selected from one or more of oleyl alcohol, ricinolyl alcohol, linolyl alcohol, linoleyl alcohol, eleosteryl alcohol, palmitoleyl alcohol, or arachidonyl alcohol in combination with (ii) an alkylene glycol selected from one or more of propylene glycol or dipropylene glycol, said alkylene glycol being present in the solvent in an amount of more than 12% by weight to provide for mutual dissolution of the unsaturated $C_{16}$–$C_{20}$-fatty acid alcohol and the active agent; and
   (b) 15–80% of a viscosity enhancing agent that is a waxy substance for imparting a solid consistency to the composition; all percentages in (a) and (b) being based on the total weight of the homogeneous carrier system.

2. The composition according to claim 1, wherein the amount of said alkylene glycol is at least 15% by weight.

3. The composition according to claim 1, wherein the biologically active agent comprises a lipophilic compound.

4. The composition according to claim 3, wherein the biologically active compound is selected from the group consisting of steroids, sex hormones, vitamins, biologically active lipids, fatty acids, antivirals, antibacterials, antiprotozoals, antifungals, and local anesthetics.

5. The composition as claimed in according to claim 4, wherein the biologically active compound is selected from fluocinonide, omega-3-fatty acids azelaic acid, and salts and esters thereof.

6. The composition according to claim 4, wherein the biologically active compound is clobetasol or a salt or an ester thereof.

7. The composition according to claim 1, wherein the alkylene glycol is propylene glycol.

8. The composition according to claim 1, wherein the solvent additionally comprises propyl myristate, palmitate, isopropylpalmitate, stearate, propyl ester of sorbic acid and combinations thereof.

9. The composition according to claim 8, wherein said additional solvent is isopropylpalmitate.

10. The composition according to claim 1, wherein the waxy substance comprises a natural or synthetic wax, a fat, a glycol ester of a $C_{18}$–$C_{36}$ fatty acid, or a mixture of two or more thereof.

11. The composition according to claim 10, wherein the waxy substance comprises a combination of a natural or synthetic wax and one or a combination of a triglyceride or a glycol ester.

12. The composition according to claim 1, wherein the amount of solvent is within the range of 25–75% by weight, and the amount of viscosity enhancing agent is within the range of 15–55%, based on the total weight of the homogeneous carrier system.

13. The composition according to claim 1, wherein the amount of said alkylene glycol is within the range of 12–23% by weight, based on the total weight of the homogeneous carrier system.

14. The composition according to claim 8, wherein the weight ratio of unsaturated fatty acid: alcohol additional solvent ranges from 1:2 to 5:1.

15. The composition according to claim 1, wherein the biologically active agent is present in a concentration of up to the solubility limit thereof in the homogeneous carrier system.

16. The composition according to claim 1, wherein the concentration of the biologically active agent is 0.01–10%, by weight, based on the weight of the homogeneous carrier system.

17. The composition according to claim 1, wherein said composition is a stick.

18. The composition according to claim 1, wherein the biologically active agent is a therapeutically or prophylactically active agent.

19. The composition according to claim 18, for topical application to the skin of a mammal, said composition having a viscosity that is adapted for said application.

20. A process for the preparation of a biologically active composition according to claim 1, comprising: dissolving the biologically active agent in said solvent therefor; combining the resulting solution with a viscosity enhancing agent so as to impart a solid consistency to said solution; and shaping the resulting composition into a desired form.

21. A method of prophylactic or therapeutic treatment of a dermatological condition comprising: topically applying a prophylactically or therapeutically effective amount of an active agent containing the solid composition according to claim 1, wherein the active agent is an agent for treatment or prophylaxis of a dermatological condition.

22. The method according to claim 21, wherein the active agent is selected from the group consisting of a steroid, vitamin, biologically active lipid, fatty acid, antimicrobial, and anesthetic.

23. The method according to claim 21, wherein the active agent is selected from the group consisting of a corticosteroid, sex hormone, vitamin A, vitamin D2, vitamin D3, vitamin E, vitamin K, an antibiotic, an antiviral, an antiprotozoal, an antifungal, and an amide local anesthetic.

24. The method according to claim 21, wherein the active agent is selected from the group consisting of clobetasol or a salt or ether thereof and beta-methasone, or a salt or ester thereof.

25. The method according to claim 24, wherein the active agent is clobetasol proprionate, methasone-17-valerate, or beta-methasone diproprionate.

26. The composition according to claim 1, wherein the biologically active agent is a lipophilic drug.

27. A composition according to claim 3, wherein the biologically active compound is a lipophilic anesthetic of the amide type.

28. A composition according to claim 6, wherein the biologically active compound is clobetasol propionate.

29. The composition according to claim 1, wherein the waxy substance comprises a natural or a synthetic wax that is a monoester of a long-chain carboxylic acid with a long-chain alcohol, and the fat is a triglyceride of a $C_{18}$–$C_{36}$ fatty acid.

30. The composition according to claim 1, wherein the amount of said alkylene glycol ranges from 15–23% by weight, based on the total weight of the homogeneous carrier system.

31. The composition according to claim 1, wherein the amount of said alkylene glycol ranges from 12–20% by weight, based on the total weight of the homogeneous carrier system.

32. The composition according to claim 1, wherein the amount of said alkylene glycol ranges from ranges from 15–20% by weight, based on the total weight of the homogeneous carrier system.

33. The composition according to claim 8, wherein the weight ratio of unsaturated fatty acid alcohol: additional solvent is within the range of 1:2 to 3:1.

34. The composition according to claim 8, wherein the weight ratio of unsaturated fatty acid alcohol: additional solvent is within the range of 1:2 to 2:1.

35. The composition according to claim 1, wherein the concentration of the biologically active agent is 0.02–5% by weight based on the weight of the homogeneous carrier system.

36. The composition according to claim 1, wherein the biologically active compound is betamethasone, or a salt or ester thereof.

37. The composition according to claim 1, wherein the biologically active compound is beta-methasone-17-valerate or beta-methasone diproprionate.

38. The composition according to claim 4, wherein the steroid is a corticosteroid.

39. The compound according to claim 4, wherein the sex hormone is selected from the group consisting of androgens, estrogens and derivatives thereof.

40. The compound according to claim 4, wherein the vitamin is selected from the group consisting of vitamin A, vitamin D2, vitamin D3, vitamin E and vitamin K.

* * * * *